United States Patent
Xu et al.

(10) Patent No.: US 11,344,849 B2
(45) Date of Patent: May 31, 2022

(54) FILTRATION CELL AND METHOD FOR FILTERING A BIOLOGICAL SAMPLE

(71) Applicant: Becton, Dickinson and Company, Franklin Lakes, NJ (US)

(72) Inventors: Qihua Xu, Cary, NC (US); Alexander G. Lastovich, Raleigh, NC (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 15/565,307

(22) PCT Filed: Jun. 7, 2016

(86) PCT No.: PCT/US2016/036200
§ 371 (c)(1),
(2) Date: Oct. 9, 2017

(87) PCT Pub. No.: WO2016/200800
PCT Pub. Date: Dec. 15, 2016

(65) Prior Publication Data
US 2018/0071689 A1    Mar. 15, 2018

Related U.S. Application Data

(60) Provisional application No. 62/172,445, filed on Jun. 8, 2015.

(51) Int. Cl.
*B01D 61/18*    (2006.01)
*B01D 63/08*    (2006.01)
(Continued)

(52) U.S. Cl.
CPC ......... *B01D 67/0032* (2013.01); *A61M 1/365* (2014.02); *A61M 1/3644* (2014.02);
(Continued)

(58) Field of Classification Search
CPC combination set(s) only.
See application file for complete search history.

(56) References Cited

U.S. PATENT DOCUMENTS

| 4,066,554 A | | 1/1978 | Guyer | |
| 4,212,742 A | * | 7/1980 | Solomon | B01D 63/082 |
| | | | | 210/247 |

(Continued)

FOREIGN PATENT DOCUMENTS

| EP | 0403031 A2 | 12/1990 |
| EP | 0464707 A2 | 1/1992 |

(Continued)

OTHER PUBLICATIONS

Machine Translation of KR 2002/0061895, pp. 1-4 (Year: 2002).*
(Continued)

*Primary Examiner* — Patrick Orme
(74) *Attorney, Agent, or Firm* — Botos Churchill IP Law LLP

(57) ABSTRACT

A filtration cell (10) for a biological sample including an upper chamber for receiving the biological sample to be filtered, a lower chamber in fluid communication with the upper chamber, and a filtration membrane (14) positioned between the upper chamber and the lower chamber is disclosed. A surface of the filtration membrane has a contact angle >90°. The flow of the biological sample through the upper chamber may be tangential to the filtration membrane and a filtrate passing through the filtration membrane may be collected in the lower chamber. Also, a method of filtering a biological sample including passing the biological sample through an upper chamber of a filtration cell as described above and collecting a filtrate in the lower chamber is disclosed.

5 Claims, 7 Drawing Sheets

(51) Int. Cl.
| | | |
|---|---|---|
| *B01D 71/50* | (2006.01) | |
| *B01D 61/14* | (2006.01) | |
| *A61M 1/34* | (2006.01) | |
| *B01D 67/00* | (2006.01) | |
| *A61M 1/36* | (2006.01) | |
| *A61M 1/16* | (2006.01) | |

(52) U.S. Cl.
CPC .......... *B01D 61/147* (2013.01); *B01D 61/18* (2013.01); *B01D 63/087* (2013.01); *B01D 71/50* (2013.01); *A61M 1/1621* (2014.02); *A61M 1/1631* (2014.02); *A61M 1/3496* (2013.01); *A61M 1/3643* (2013.01); *A61M 2202/0415* (2013.01); *B01D 2321/2066* (2013.01); *B01D 2321/2083* (2013.01); *B01D 2323/04* (2013.01); *B01D 2325/38* (2013.01)

(56) References Cited

U.S. PATENT DOCUMENTS

| | | | |
|---|---|---|---|
| 4,343,705 A | 8/1982 | Legg | |
| 4,740,313 A | 4/1988 | Schoendorfer et al. | |
| 4,769,150 A * | 9/1988 | Ramstack | A61M 1/3496 |
| | | | 210/636 |
| 4,871,462 A | 10/1989 | Fischel et al. | |
| 4,980,297 A | 12/1990 | Haynes et al. | |
| 5,034,135 A | 7/1991 | Fischel | |
| 5,100,376 A | 3/1992 | Blake | |
| 5,922,210 A * | 7/1999 | Brody | B01D 39/1692 |
| | | | 210/416.1 |
| 6,010,627 A | 1/2000 | Hood | |
| 6,153,104 A | 11/2000 | Robertson | |
| 8,889,071 B2 | 11/2014 | Aota et al. | |
| 2004/0251214 A1 | 12/2004 | Adams | |
| 2005/0261642 A1 | 11/2005 | Weston | |
| 2007/0151924 A1* | 7/2007 | Mir | B01D 61/14 |
| | | | 210/637 |
| 2008/0272283 A1 | 11/2008 | Feldsine et al. | |
| 2010/0285573 A1* | 11/2010 | Leck | B01L 3/5088 |
| | | | 435/288.4 |
| 2011/0058983 A1 | 3/2011 | Chastenet et al. | |
| 2011/0155667 A1 | 6/2011 | Charest | |
| 2012/0291867 A1 | 11/2012 | Gassman | |
| 2013/0015119 A1* | 1/2013 | Pugh | B01D 63/087 |
| | | | 210/321.6 |
| 2013/0334139 A1 | 12/2013 | Blickhan | |
| 2014/0042094 A1 | 2/2014 | Montagu | |
| 2014/0217027 A1 | 8/2014 | Meyer | |
| 2014/0305196 A1 | 10/2014 | Ellis et al. | |
| 2014/0305197 A1 | 10/2014 | Fletcher et al. | |
| 2014/0308167 A1 | 10/2014 | Fletcher et al. | |
| 2014/0309556 A1 | 10/2014 | Fletcher et al. | |
| 2015/0060363 A1 | 3/2015 | Fletcher et al. | |
| 2015/0152467 A1 | 6/2015 | Ingber et al. | |
| 2016/0074569 A1* | 3/2016 | Schuetz | G01N 33/491 |
| | | | 210/650 |

FOREIGN PATENT DOCUMENTS

| | | | | |
|---|---|---|---|---|
| EP | 2516320 A1 | 10/2012 | | |
| EP | 2842619 A1 | 3/2015 | | |
| JP | 57104862 | 6/1982 | | |
| JP | S57104862 A | 6/1982 | | |
| JP | S61172060 A | 8/1986 | | |
| JP | S63224703 A | 9/1988 | | |
| JP | HEI03247345 | 11/1991 | | |
| JP | H0910299 A | 1/1997 | | |
| JP | H10-28727 A | 2/1998 | | |
| JP | H10-180179 A | 7/1998 | | |
| JP | 2010237050 A | 10/2003 | | |
| JP | 2004503745 A | 2/2004 | | |
| JP | 2005529746 A | 10/2005 | | |
| JP | 2014523534 A | 9/2014 | | |
| KR | 20020061895 * | 7/2002 | ............ | B01D 69/12 |
| KR | 20020061895 A | 7/2002 | | |
| WO | 19910001796 A1 | 2/1991 | | |
| WO | 9614578 A1 | 5/1996 | | |
| WO | 9624425 A1 | 8/1996 | | |
| WO | WO 96/24425 * | 8/1996 | ............ | B01D 35/00 |
| WO | 20000050157 A1 | 8/2000 | | |
| WO | 0112325 A1 | 2/2001 | | |
| WO | 2011079217 A1 | 6/2011 | | |
| WO | 2012125460 A1 | 9/2012 | | |
| WO | 2013008142 A1 | 1/2013 | | |
| WO | 2014023765 A2 | 2/2014 | | |
| WO | 2014095058 A1 | 6/2014 | | |
| WO | 2015014934 A1 | 2/2015 | | |
| WO | WO 2015/014934 * | 2/2015 | ............ | A61M 1/02 |
| WO | 2016200806 A1 | 12/2016 | | |

OTHER PUBLICATIONS

KR20020061895A (Google Machine Translation) (Year: 2021).*
Japanese Office Action issued in corresponding JP application No. 2017-564128 dated Nov. 13, 2018, pp. 5.
Office Action received in corresponding EP Appl. No. 16731437.6 dated Sep. 4, 2020 (6 pages).
Office Action from European Patent Office received European App. No. 16731437.6 dated Jan. 15, 2020, 5 pages.
Chinese Office Action received in 201780048849.8 dated Nov. 21, 2019, pp. 15.
International Search Report and Written Opinion for Application No. PCT/US2017/036747 dated Nov. 21, 2017.
ISR and Written Opinion for Application No. PCT/US2016/036209 dated Aug. 25, 2016.
Jaffrin My: Innovative Processes for Membrane Plasma Separation 11, Journal of Membrane Science, Elsevier BV, NL, vol. 44, No. 1, Jun. 1, 1989 (Jun. 1, 1989), pp. 115-129, XP000068839, ISSN: 0376-7388, DOI: 10.1016/S0376-7388(00)82344-3, pp. 123-124.
Japanese Official Notice of Rejection issued in corresponding JP application No. 2017-563527 dated Oct. 23, 2018.
Wang Z F et al: "Seamless joining of porous membrane with thermoplastic microfluidic devices", Microelectronic Engineering, vol. 11 O, XP028673721, ISSN: 0167-9317, DOI: 10.1016/J.MEE. 2013.02.074, pp. 386-391.
Japanese Notice of Refusal issued in Japanese application No. 2018-545826 dated Feb. 2, 2021.
Office Action issued in corresponding Japanese Patent Application No. 2018-564216 dated Jun. 3, 2021, 8 pp.
Japanese Office Action received in JP Application No. 2020-000574, dated Mar. 2, 2021, 6 pp.
First Examination Report issued in corresponding Indian Patent Application No. 201817047315, dated May 31, 2021, 55 pp.
Office Action received in corresponding Japanese Patent Application No. 2020-000574 dated Oct. 26, 2021, pp. 10.
Office Action issued in corresponding Japanese Patent Application No. 2018-564216 dated Dec. 14, 2021, 6 pp.
Summons to Attend Oral Proceedings issued in corresponding EP Patent Application No. 16 731 437.6 dated Dec. 10, 2021, 9 pp.
Office Action issued in corresponding EP Patent Application No. 17713096.0 dated Feb. 1, 2022, 8 pp.
Office Action issued in corresponding European Patent Application No. 1773181.1 dated Apr. 4, 2022, (7 pages).

* cited by examiner

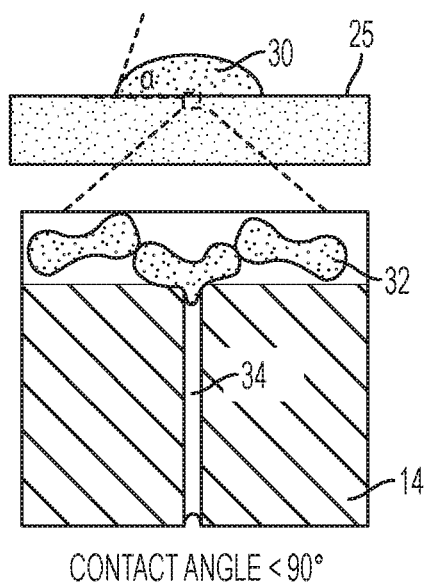
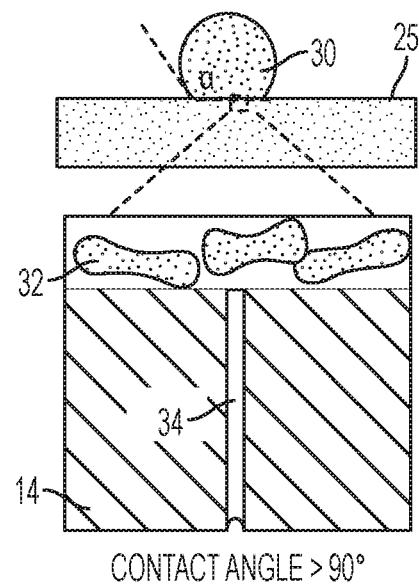
FIG. 4A
FIG. 4B

FILTRATION CELL AND METHOD FOR FILTERING A BIOLOGICAL SAMPLE

CROSS-REFERENCE TO RELATED APPLICATION

This application is the United States national phase of International Application No. PCT/US2016/036200, filed Jun. 7, 2016, entitled "Filtration Cell and Method for Filtering a Biological Sample", and claims priority to U.S. Provisional Application No. 62/172,445, filed on Jun. 8, 2015 and entitled "Plasma Extractor", the disclosure of which is incorporated by reference herein in its entirety.

BACKGROUND OF THE INVENTION

1. Field of the Invention

The present invention relates to a filtration cell and a method for filtering a biological sample and, specifically, to a filtration cell and a method for filtering plasma from a whole blood sample with minimal hemolysis.

2. Description of Related Art

Plasma separation of whole blood in sub-milliliter collection volumes (25 to 500 μm) may be necessary for various diagnostic tests. For example, near patient care or point-of-care (POC) testing requires rapidly obtained test results with small volume collection samples, for example, a blood sample collected using a capillary draw. As the overall collection sample size decreases, a need exists for high quality plasma separation having low cellular contamination, low analyte bias, and low hemolysis.

Plasma can be separated from whole blood samples using a variety of different methods including direct filtration using various filters, hydrodynamic branch flow extraction, dielectrophoresis separation, acoustic focusing, magnetic separation, and centrifugal separation in microliter amounts. However, all of these methods have various limitations. For example, many of these methods have one or more drawbacks including the need for high fold dilution, reliance on external hardware, lower plasma yield, long separation times, high cellular contamination, and significant sample hemolysis.

Track etched membranes have been used to separate plasma from whole blood. The advantage of track etched membranes is the uniform pore size and relatively small surface area as compared to other filtration membranes. The potential low non-specific binding characteristics of track etched membranes is very attractive for detecting low concentration analytes such as troponin in a cardiac patient. While direct filtration using track etched membranes is limited due to clotting, a tangential flow process has shown much better performance. A multi-pass reciprocating process using a track etched membrane to extract plasma from whole blood outperforms other cross flow hydrodynamic based technologies in plasma yield, cellular contamination, and separation time. However, the resulting plasma is often unacceptable for many testing procedures due to the resulting significant sample hemolysis.

SUMMARY OF THE INVENTION

The present invention is directed to a filtration cell for a biological sample including an upper chamber for receiving the biological sample to be filtered, a lower chamber in fluid communication with the upper chamber, and a filtration membrane positioned between the upper chamber and the lower chamber. The surface of the filtration membrane has a contact angle ≥90°. The flow of the biological sample through the upper chamber may be tangential to the filtration membrane and the filtrate passing through the filtration membrane may be collected in the lower chamber.

The filtration membrane may include a plurality of pores and the capillary force in the pores may be ≤0 psi. In certain embodiments, the contact angle may be ≤150°, such as 90-105°. The filtration membrane may be a track-etched membrane or a fibrous membrane, and may be, more specifically, a polycarbonate track etched (PCTE) membrane. The filtration membrane may be surface treated to reduce the contact angle and, more specifically, may be surface treated with a fluorosilane such as trichloro(1,1,2,2-perfluoroctyl) silane. The filtration membrane may have a plurality of pores each having a diameter of less than 2 μm.

In certain configurations, the filtration cell may also include a reciprocating unit in communication with the upper chamber for reciprocating the biological sample over at least a portion of the filtration membrane. In other configurations, a pressure unit may be configured to apply positive pressure to the biological sample within the upper chamber.

The present invention is also directed to a filtration cell including a passageway for receiving a biological sample to be filtered. The passageway may include an inlet, an outlet, and a flow channel extending therebetween. The filtration cell may also include a filtrate collection chamber and a filtration membrane positioned between the flow channel and the filtrate collection chamber. The surface of the filtration membrane may have a contact angle ≥90°. The flow of the biological sample through the flow channel may be tangential to the filtration membrane.

The filtration membrane may be a track-etched membrane or a fibrous membrane. In certain embodiments, the filtration membrane may have a plurality of pores and the capillary force in each of the pores may be ≤0 psi. The contact angle of the filtration membrane may be ≤150°, and the filtration membrane may have been surface treated to reduce the contact angle.

The filtration cell may also include a reciprocating unit in communication with the upper chamber for reciprocating the biological sample over the filtration membrane. Optionally, the filtration cell may include a pressure unit configured to apply positive pressure to the biological sample within the upper chamber.

The present invention is also directed to a method of filtering a biological sample including passing the biological sample through an upper chamber of a filtration cell, as described above, and collecting a filtrate in the lower chamber. The biological sample may be a whole blood sample and the filtrate may be a plasma portion of the whole blood sample. The biological sample may be passed through the upper chamber more than one time and positive pressure may be applied to the biological sample within the upper chamber.

The present invention is also directed to a method of filtering a biological sample including passing the biological sample through a flow channel of a filtration cell, as described above, and collecting a filtrate in the collection chamber. The biological sample may be a whole blood sample and the filtrate may be a plasma portion of the whole blood sample. The biological sample may be passed through the flow channel more than one time and positive pressure may be applied to the biological sample within the flow channel.

BRIEF DESCRIPTION OF THE DRAWINGS

FIG. 4A is a schematic diagram showing blood being filtered in a filtration cell having a filtration membrane with a contact angle <90°;

FIG. 4B is a schematic diagram showing blood being filtered in a filtration cell having a filtration membrane with a contact angle >90°;

DESCRIPTION OF THE INVENTION

The present invention is directed to a filtration cell for a biological sample and a method of filtering a biological sample, particularly when only small volumes of the biological sample are available. The biological sample may include whole blood from which a plasma portion is to be separated.

Figure 1:
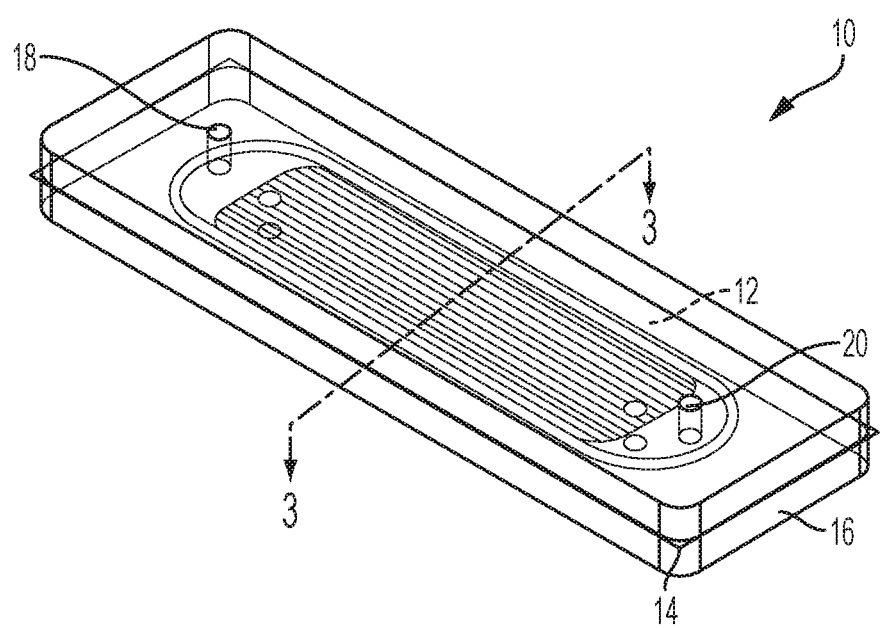
FIG. 1 is a perspective view of a filtration cell according to the present invention.
Figure 2:
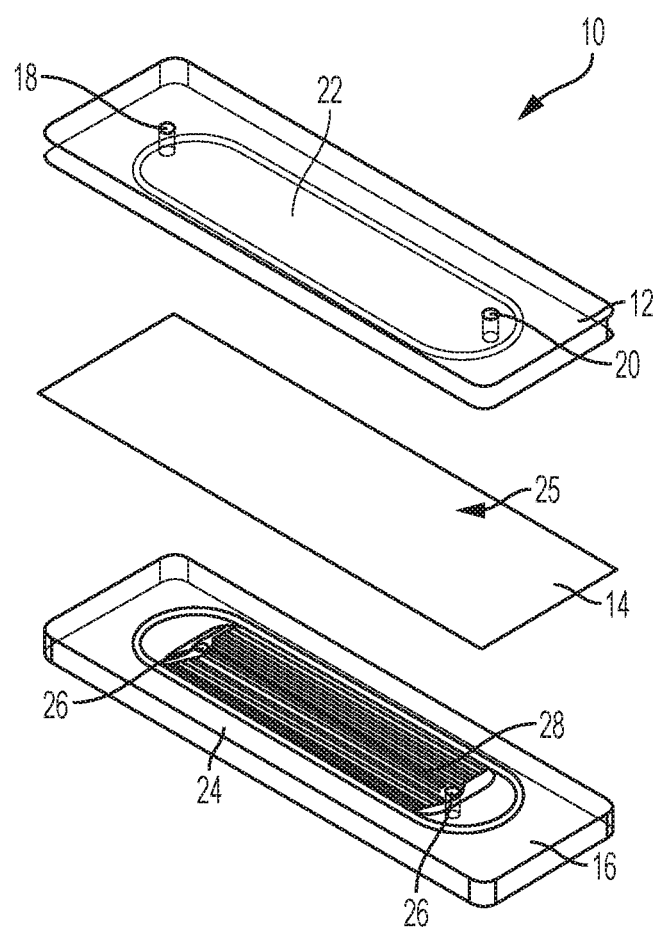
FIG. 2 is an expanded perspective view of a filtration cell according to the present invention.
Figure 3:
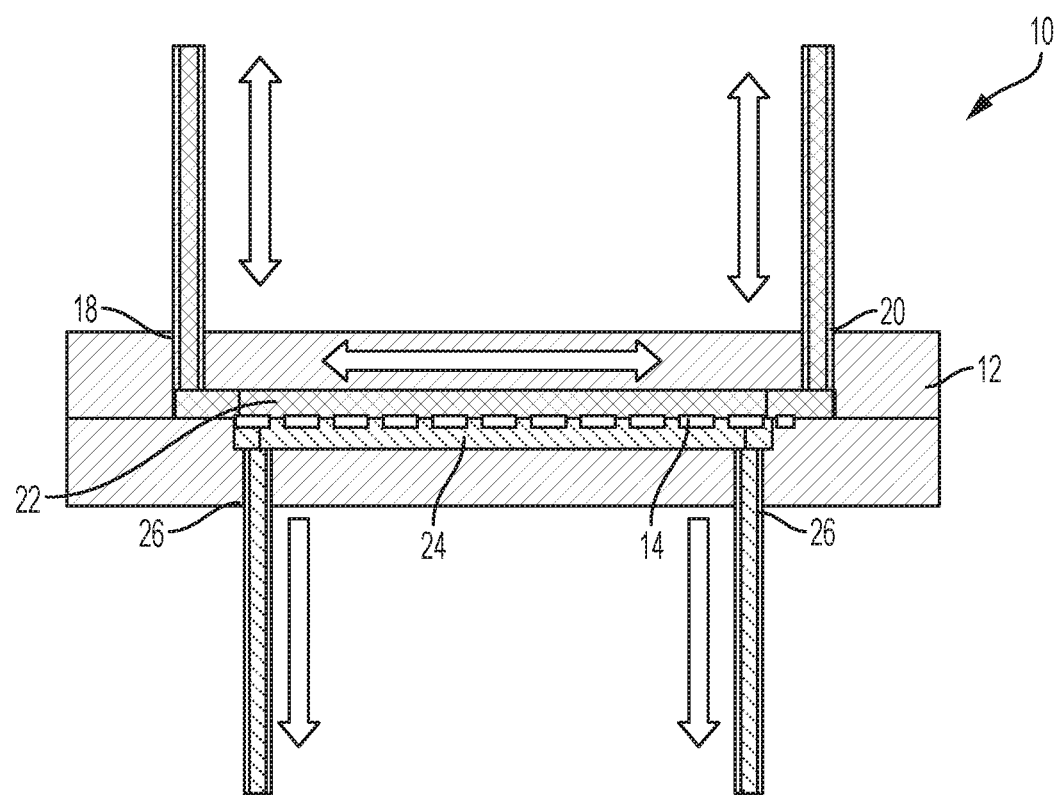
FIG. 3 is a cross-sectional view of a filtration cell of FIG. 1, taken along line 3-3, according to the present invention.

As shown in FIGS. 1-3, a filtration cell 10 includes a cover 12, a filtration membrane 14, and a base 16. The filtration membrane 14 is disposed between the cover 12 and the base 16.

The cover 12 has a first opening 18 and a second opening 20 extending therethrough. An upper chamber 22 is in fluid communication with and extends between the first opening 18 and the second opening 20 and above the filtration membrane 14.

The base 16 includes a lower chamber 24 having a least one outlet 26 extending through the bottom surface of the base 16. The embodiment shown in FIGS. 1-3 has two outlets 26, one at each end of the lower chamber 24. The lower chamber 24 may also include ridges 28 forming channels within the lower chamber 24 and providing support to the filtration membrane 14.

The upper chamber 22 and the lower chamber 24 are in fluid communication with one another through the filtration membrane 14. The upper chamber 22 and the lower chamber 24 may have substantially the same size and shape and be positioned adjacent each another with the filtration membrane 14 separating the upper chamber 2 and the lower chamber 24.

The filtration membrane 14 may have substantially the same shape and size as the cover 12 and the base 16 as shown in FIGS. 1 and 2, or may have any shape and/or size sufficient to separate the upper chamber 22 from the lower chamber 24.

The filtration membrane 14 may be made from any suitable material capable of filtering the biological sample including, but not limited to fibrous membranes and track etched membranes. For example, the filtration membrane 14 may be made from a track-etched membrane comprising a thin film including discrete pores. In certain embodiments, the film may be formed through a combination of charged particle bombardment or irradiation and chemical etching providing increased control over the pore size and density. More specifically, the filtration membrane 14 may be a polycarbonate track-etched membrane (PCTE membrane). The filtration membrane 14 may have a pore size of 0.4 μm. In certain configurations, a track-etched membrane may have a thickness of about 10-12 μm. In other configurations, a fibrous membrane may have a thickness of >100 μm. In many samples separation procedures, a thinner membrane requires smaller initial sample collection volumes.

In one configuration, at least the upper surface 25 of the filtration membrane 14 facing the upper chamber 22 has a contact angle α of ≥90°, preferably the contact angle α is ≤150°, and more preferably the contact angle α is between 90-105°. As shown in FIGS. 4A and 4B, the contact angle is defined in the conventional sense as the angle α formed by the solid surface of the filtration membrane 14 and the tangent of a droplet 30 of the liquid sample on the surface of the filtration membrane 14.

A filtration membrane having a contact angle of ≥90° can be achieved by making the filtration membrane from, or treating the filtration membrane with, a hydrophobic material. Such material include but are not limited to, those shown in Table 1.

TABLE 1

| Material | Contact Angle |
| --- | --- |
| trichloro(1,1,2,2-perfluorooctyl) silane | |
| heptadecafluorodecyltrimethoxysilane | 115° |
| poly(tetrafluoroethylene) | 108-112° |
| poly(propylene) | 108° |
| octadecyldimethylchlorosilane | 110° |
| octadecyltrichlorosilane* | 102-109° |
| tris(trimethylsiloxy)silylethyldimethylchlorosilane | 104° |
| octyldimethylchlorosilane | 104° |
| dimethyldichlorosilane | 95-105° |
| butyldimethylchlorosilane | 100° |
| trimethylchlorosilane | 90-100° |
| poly(ethylene) | 88-103° |
| poly(styrene) | 94° |
| poly(chlorotrifluoroethylene) | 90° |

The filtration membrane 14, such as a PCTE membrane, can be treated using such materials in either the gas phase or liquid phase.

In one embodiment, a reciprocating unit is attached to the first opening 18 and the second opening 20. The reciprocating unit reciprocates the biological sample back and forth through the upper chamber 22 and tangentially over the filtration membrane 14. Reciprocation may be accomplished by any suitable reciprocating unit.

A pressure unit may also be provided to apply positive pressure to the biological sample within the upper chamber and maintain a given trans-membrane pressure within the filtration cell 10. The positive pressure may be applied using any suitable pressure unit.

Alternatively, other hydrophobic treatments such as creating nano/micro features on the surface of the filtration membrane 14, such as blood-phobic surfaces, may be used. Such surface structures can create hydrophobic surfaces with a contact angle of 140° or higher.

In use, a biological sample is introduced into the filtration cell 10 through the first opening 18. The sample flows through the upper chamber 22 to the second opening 20. The sample is then reciprocated back and forth between the first opening 18 and the second opening 20 passing through the upper chamber 22 in a flow that is tangential to the filtration membrane 14. The sample may be passed across through the upper chamber 22 and across the filtration membrane 14 any suitable number of times to affect filtration of the sample. As the sample passes across the filtration membrane 14, the filtrate is collected in the lower chamber 24. The filtrate may pass continually out of the lower chamber 24 through the outlet 26 into a collection device or may be held in the lower chamber 24 by a stopper or valve acting to limit flow through the outlet 26.

The filtration cell for a biological sample and the method of filtering a biological sample will now be explained with respect to the filtration of plasma from whole blood.

If the filtration cell 10 has a filtration membrane 14 having a contact angle <90°, severe hemolysis occurs when red blood cells 32 are drawn into pores 34 of the filtration membrane 14, as shown schematically in FIG. 4A. When the red blood cells 32 are drawn into the pores 34 they are subject to rupturing and releasing their contents into the plasma.

It has been found that by priming the filtration cell with a liquid and tightly controlling the sample inlet/outlet pressure, the hemolysis can be reduced.

Blood samples were filtered in a filtration cell having a filtration membrane with a contact angle of <90° using 50 passes of reciprocating flow at a differential pressure (Δp) of 0.4 psi to drive the tangential flow through the upper chamber and across the filtration membrane. One set of samples was filtered at a trans-membrane pressure of 3 psi after priming the filtration membrane with a solution of phosphate-buffered saline (PBS) with 1% bovine serum albumin (BSA), one set of samples was filtered at a trans-membrane pressure of 0.7 psi after priming the filtration membrane with a solution of phosphate-buffered saline (PBS) with 1% bovine serum albumin (BSA), and one set of samples was filtered at a trans-membrane pressure of 0.7 psi without priming. The results are shown in Table 2.

TABLE 2

| Sample Set | Priming | Trans-Membrane Pressure (psi) | Hemoglobin Concentration (HGB) in Plasma After Filtration (mg/dL) |
|---|---|---|---|
| 1 | Yes | 3 | 50-160 |
| 2 | No | 0.7 | 60-300 |
| 3 | Yes | 0.7 | 5-16 |

As can be seen from the results identified in Table 2, when the contact angle of the filtration membrane is <90°, priming the filtration membrane and carefully controlling the trans-membrane pressure are both necessary to keep hemolysis low.

Figure 5:
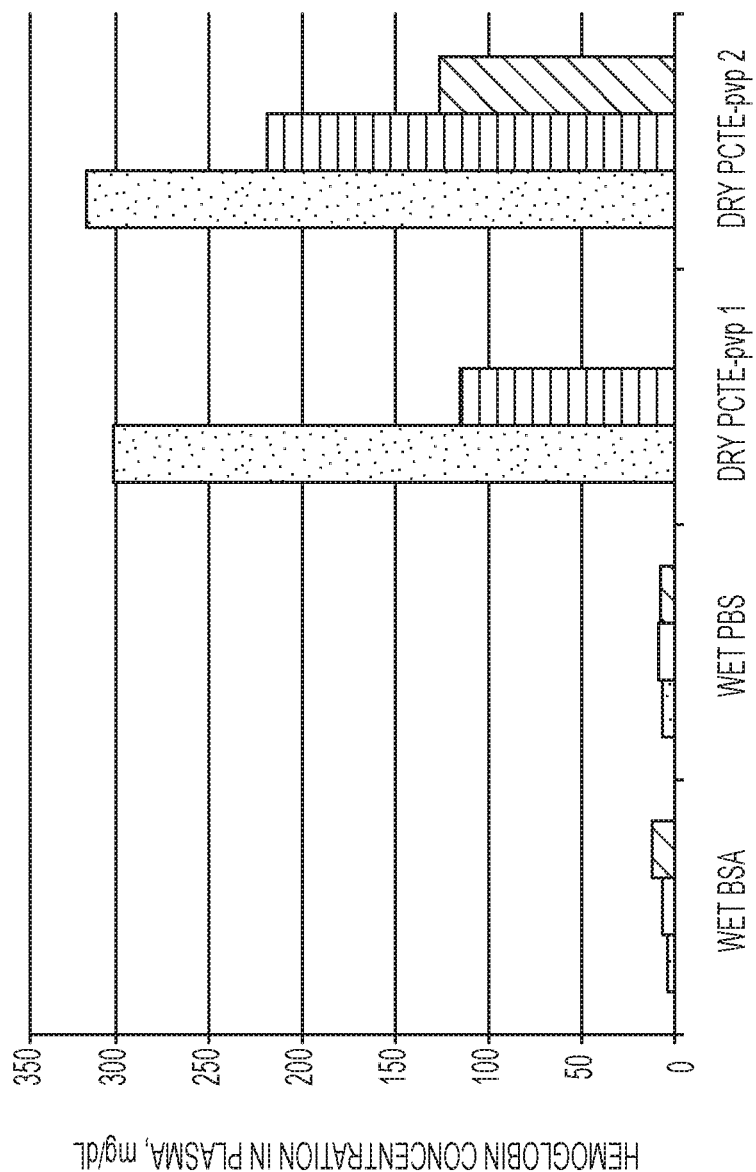
FIG. 5 is a graph showing hemolysis results for primed (wet) and unprimed (dry) filtration membranes.

Repeated testing using primed (wet) and unprimed (dry) filtration membranes confirmed the reduction in hemolysis when using primed filtration membranes. The results are shown in FIG. 5.

However, priming the device with a liquid presents numerous practical challenges. The design of the filtration cell and the filtering process are both more complex. The shelf life of the filtration cell can be short if the priming liquid is pre-packaged in or with the filtration cell. The plasma sample can be inconsistently diluted due to input volume variation of the priming liquid which could lead to alteration of test results. Some analytes may no longer be detectable due to dilution caused by the priming liquid. Accordingly, a filtration membrane that must be primed and which requires carefully controlling the trans-membrane pressure, is less desirable in most configurations.

Figure 6:
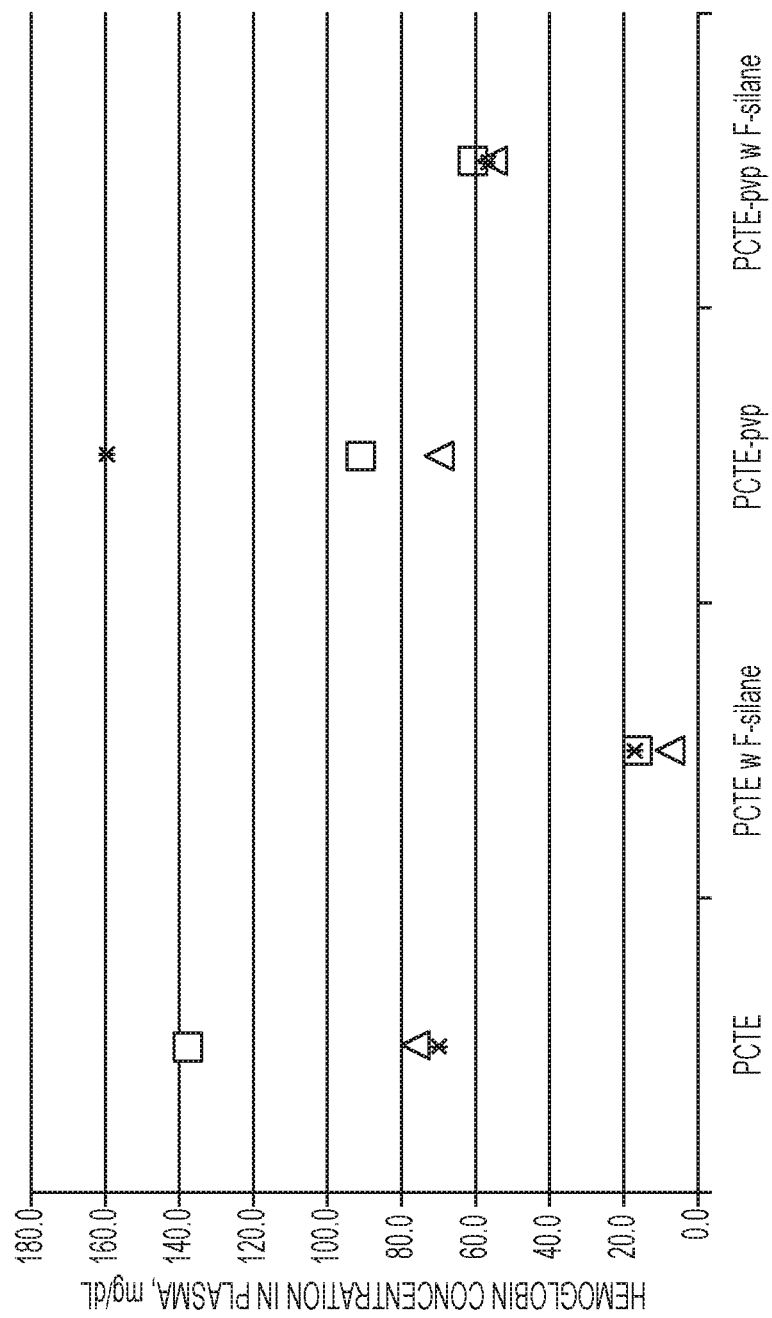
FIG. 6 is a graph showing hemolysis results for surface treated and untreated filtration membranes.

Samples were then filtered using filtration membranes that were pre-treated with a fluorosilane (trichloro(1,1,2,2-perfluorooctyl) silane treatment and compared to samples filtered with filtration membranes that received no pre-treatment. Both polycarbonate track-etched (PCTE) membranes and polyvinyl pyridine coated polycarbonate track-etched (PCTE-pvp) membranes having a pore size of 0.4 μm were used. Filtration consisted of 50 passes of reciprocating flow at a trans-membrane pressure of 0.7 psi. Each type of membrane was tested three times. The results are given in Table 3 and shown visually in FIG. 6.

TABLE 3

| Filtration membrane | Contact Angle | Capillary Force (psi) | Hemoglobin Concentration (HGB) in Plasma After Filtration (mg/dL) | | | |
|---|---|---|---|---|---|---|
| | | | Sample 1 | Sample 2 | Sample 3 | Average |
| PCTE | 88 | 1.82 | 73.6 | 138.3 | 78.5 | 96.8 |
| PCTE treated with F-silane | 99 | −8.06 | 18.6 | 17.7 | 13.6 | 16.6 |
| PCTE-pvp | 56 | 29.1 | 159.7 | 91.0 | 69.8 | 106.8 |
| PCTE-pvp treated with F-silane | 68 | 19.5 | 56.3 | 61.0 | 55.3 | 57.5 |

As can be seen from the results identified in Table 3, the surface treatment with fluorosilane altered the contact angle of the filtration membrane and reduced hemolysis.

Figure 7:
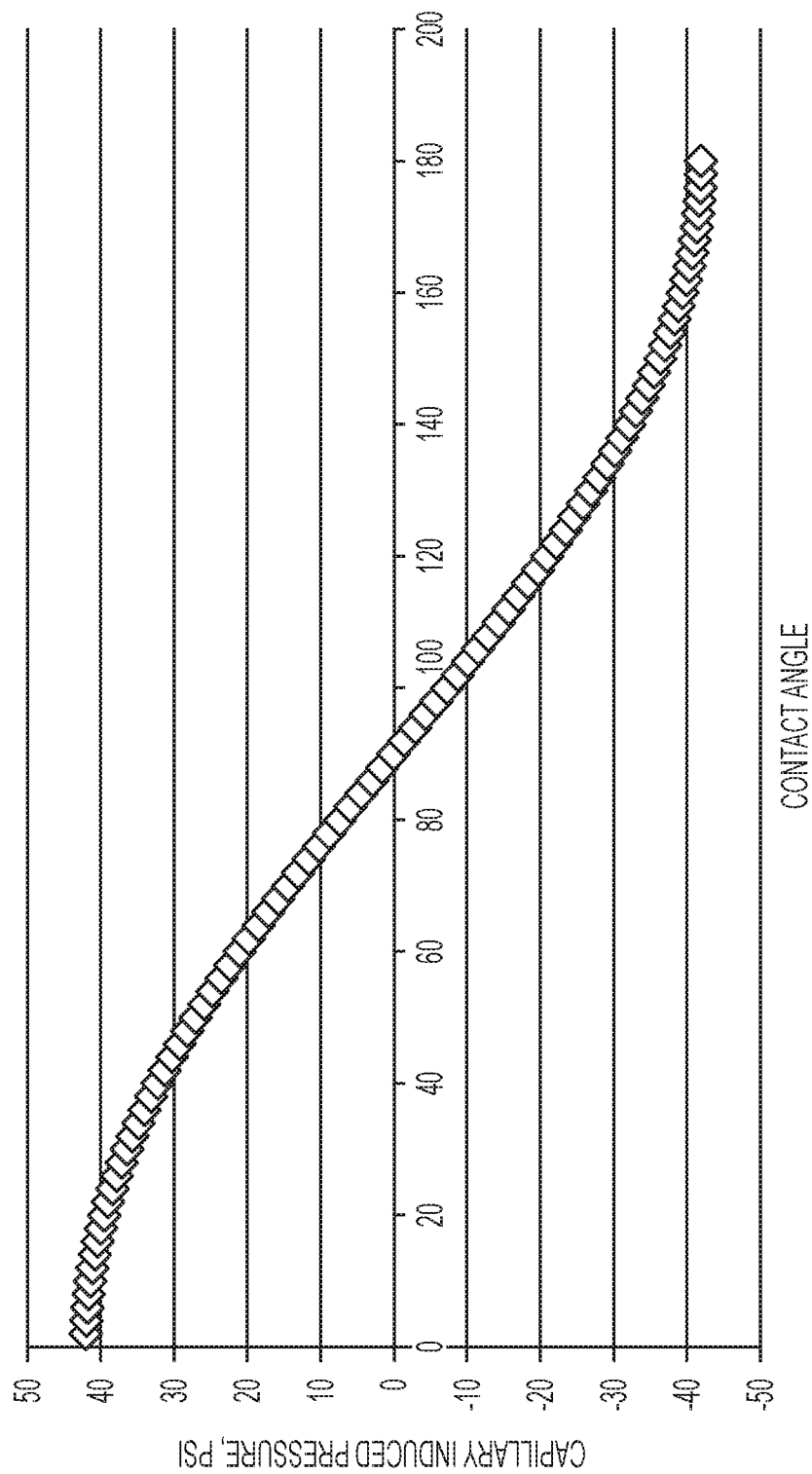
FIG. 7 is a graph showing the effect of contact angle on capillary force for a filtration membrane having a 0.4 μm pore size.

Capillary force in the pores of the filtration membrane can be expressed by the following equation when liquid is contacted with the filtration membrane:

$$\text{Capillary Force} = \frac{2\gamma\cos\alpha}{r}$$

where γ is the surface tension of the liquid, α is the contact angle of the liquid on the solid surface, and r is the radius of the filtration membrane pore (capillary). Surface tension of blood at room temperature is estimated to be around 0.058 N/m (0.072 N/m for water). With a track-etched membrane having 0.4 μm pores, the capillary force can be calculated and plotted as a function of contact angle as shown in FIG. 7. It can be seen that when the contact angle of the filtration membrane is ≥90°, there is no longer a positive capillary force acting on the red blood cells and drawing them into the pores. Therefore, having a hydrophobic surface on the filtration membrane with a contact angle ≥90° reduces hemolysis.

The contact angle of deionized water on the above-treated membranes was measured and the capillary forces were calculated (Table 3). The difference in contact angle by using deionized water instead of blood is expected to be minimal.

As can be seen, treatment with trichloro(1,1,2,2-perfluorooctyl) silane is effective to drive the contact angle larger than 90° and reduce the capillary force.

By using a filtration membrane with a contact angle ≥90° hemolysis is greatly decreased and priming of the filter, along with the associated effects, can be avoided.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A filtration cell for a biological sample comprising:
a cover comprising a first opening and a second opening;
a base comprising a least one outlet;
a filtration membrane interposed between the cover and the base, the cover and the membrane defining an upper chamber for receiving the biological sample to be filtered wherein the biological sample comprises red blood cells;
a pressure unit in communication with the upper chamber, wherein the pressure unit applies positive pressure to the biological sample within the upper chamber;
the filtration membrane and the base defining a lower chamber in fluid communication with the upper chamber; wherein the filtration membrane separates the upper chamber from the lower chamber and wherein a flow of the biological sample through the upper chamber is tangential to the filtration membrane;
a reciprocating unit in communication with the upper chamber, wherein the reciprocating unit reciprocates the biological sample over the filtration membrane;
wherein the filtration membrane comprises a polycarbonate track-etched membrane and a plurality of pores having a diameter of 0.4 μm that provide a capillary force in each of the pores that is <0 psi when the biological sample is in contact with the filtration membrane and wherein the polycarbonate track-etched membrane is treated with a fluorosilane;
and wherein a surface of the filtration membrane is hydrophobic and forms a contact angle ≥90° with liquid droplets in the sample.

2. The filtration cell of claim 1, wherein a whole blood sample is provided in the upper chamber and a separated plasma portion is collected in the lower chamber.

3. The filtration cell of claim 1, wherein the contact angle is <150°.

4. The filtration cell of claim 1, wherein the contact angle is 90°-105°.

5. The filtration cell of claim 1, wherein the fluorosilane is trichloro (1,1,2,2-perfluoroctyl) silane.

* * * * *